US00PP25283P2

(12) United States Plant Patent
van der Horst

(10) Patent No.: US PP25,283 P2
(45) Date of Patent: Feb. 3, 2015

(54) ***HELLEBORUS* PLANT NAMED 'NVDH 100'**

(50) Latin Name: *Helleborus×hybridus*
Varietal Denomination: NVDH 100

(71) Applicant: Nis van der Horst, Maastricht (NL)

(72) Inventor: Nis van der Horst, Maastricht (NL)

( * ) Notice: Subject to any disclaimer, the term of this patent is extended or adjusted under 35 U.S.C. 154(b) by 118 days.

(21) Appl. No.: 13/815,472

(22) Filed: Mar. 5, 2013

(51) Int. Cl.
*A01H 5/00* (2006.01)

(52) U.S. Cl.
USPC ..... Plt./439

(58) Field of Classification Search
USPC ..... Plt./439
See application file for complete search history.

*Primary Examiner* — Annette Para
(74) *Attorney, Agent, or Firm* — C. A. Whealy

(57) ABSTRACT

A new and distinct cultivar of *Helleborus* plant named 'NVDH 100', characterized by its upright and mounding plant habit; uniform and freely flowering habit; dark green-colored leaves; double white and yellow green-colored flowers; and good garden performance.

2 Drawing Sheets

Botanical designation: *Helleborus×hybridus.*
Cultivar denomination: 'NVDH 100'.

BACKGROUND OF THE INVENTION

The present invention relates to a new and distinct cultivar of *Helleborus* plant, botanically known as *Helleborus×hybridus* and hereinafter referred to by the name 'NVDH 100'.

The new *Helleborus* plant is a product of a planned breeding program in Maastricht, The Netherlands. The objective of the breeding program was to create new uniform *Helleborus* plants with unique leaf and flower coloration and resistance to pathogens and pests.

The new *Helleborus* plant originated from a cross-pollination conducted by the Inventor in Maastricht, The Netherlands in February, 1997 of two unnamed proprietary seedling selections of *Helleborus×hybridus*, not patented. The new *Helleborus* plant was discovered and selected by the Inventor as a single flowering plant from within the progeny of the stated cross-pollination grown in a controlled greenhouse environment in Maastricht, The Netherlands in March, 1999.

Asexual reproduction of the new *Helleborus* plant by divisions in a controlled greenhouse environment in Maastricht, The Netherlands since November, 2002 has shown that the unique features of this new *Helleborus* plant are stable and reproduced true to type in successive generations.

SUMMARY OF THE INVENTION

Plants of the new *Helleborus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'NVDH 100'. These characteristics in combination distinguish 'NVDH 100' as a new and distinct *Helleborus* plant:

1. Upright and mounding plant habit.
2. Uniform and freely flowering habit.
3. Dark green-colored leaves.

4. Double white and yellow green-colored flowers.
5. Good garden performance.

Compared to plants of the parent selections, plants of the new *Helleborus* are more uniformly mounded and are more freely flowering.

Plants of the new *Helleborus* can be compared to plants of *Helleborus orientalis* 'HLR 160', disclosed in U.S. Plant Pat. No. 21,504. In side-by-side comparisons conducted in Maastricht, The Netherlands, plants of the new *Helleborus* differed from plants of 'HLR 160' in the following characteristics:

1. Plants of the new *Helleborus* had double-type flowers whereas plants of 'HLR 160' had single-type flowers.
2. Plants of the new *Helleborus* and 'HLR 160' differed in flower color as plants of 'HLR 160' had white and greyed purple bi-colored flowers.

Plants of the new *Helleborus* can also be compared to plants of *Helleborus orientalis* 'HLR 180', disclosed in U.S. Plant Pat. No. 22,020. In side-by-side comparisons conducted in Maastricht, The Netherlands, plants of the new *Helleborus* differed from plants of 'HLR 180' in the following characteristics:

1. Plants of the new *Helleborus* had double-type flowers whereas plants of 'HLR 180' had single-type flowers.
2. Plants of the new *Helleborus* and 'HLR 180' differed in flower color as plants of 'HLR 180' had white-colored flowers with red purple-colored central spots.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'NVDH 100' grown in a container.

The photograph on the second sheet is a close-up view of a typical flower of 'NVDH 100'.

DETAILED BOTANICAL DESCRIPTION

The aforementioned photographs and following observations, measurements and values describe plants grown during the autumn in 15-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Helleborus hybridus* 'NVDH 100'.

Parentage:

*Female, or seed, parent*.—Unnamed proprietary seedling selection of *Helleborus×hybridus*, not patented.

*Male, or pollen, parent*.—Unnamed proprietary seedling selection of *Helleborus×hybridus*, not patented.

Propagation:

*Type*.—By tissue culture.

*Time to initiate roots, winter*.—About two months at 12° C.

*Time to produce a rooted young plant, winter*.—About six months at 4° C. to 15° C.

*Root description*.—Thick to thin, fleshy; white to brown in color.

*Rooting habit*.—Sparse.

Plant description:

*Plant and growth habit*.—Herbaceous perennial; upright and mounding plant habit with flowers held above the foliar plane; plant shape is roughly broadly ovate; moderately vigorous growth habit.

*Plant height*.—About 31.6 cm.

*Plant diameter* (*area of spread*).—About 34.4 cm.

Leaf description:

*Arrangement*.—Leaves arranged alternately in a basal rosette; leaves palmately compound with about five leaflets per leaf.

*Leaf length*.—About 19.3 cm.

*Leaf width*.—About 20.1 cm.

*Leaflet length*.—About 12.5 cm.

*Leaflet width*.—About 5.4 cm.

*Leaf shape*.—Palmate; orbicular in outline.

*Leaflet shape*.—Broadly elliptic to obovate.

*Leaflet apex*.—Acute to broadly acute.

*Leaflet base*.—Cuneate.

*Leaflet margin*.—Sharply serrate; somewhat undulate.

*Leaflet texture, upper and lower surfaces*.—Smooth, glabrous; leathery.

*Leaflet venation pattern*.—Pinnate.

*Leaflet color*.—Developing leaves, upper surface: Close to 137A. Developing leaves, lower surface: Close to 146B. Fully developed leaves, upper surface: Darker than between N137A and 147A; venation, close to 144B tinged at the leaf base with close to 200B to 200C. Fully developed leaves, lower surface: Close to 147A to 147B; venation, close to 145A to 145B.

*Petioles*.—Length: About 14.4 cm. Diameter: About 5 mm. Texture, upper and lower surfaces: Smooth, glabrous. Color, upper and lower surfaces: Close to 143B; at the base, close to N186C and 200B.

Flower description:

*Flower shape and habit*.—Double-type rotate flowers arranged in terminal and axillary panicles; freely flowering habit with typically about five flowers per panicle; flowers facing outwardly to nodding.

*Fragrance*.—None detected.

*Natural flowering season*.—Plants begin flowering about ten months after planting; plants flower from late autumn into the winter in Germany.

*Flower longevity on the plant*.—About ten days; flowers persistent.

*Inflorescence height*.—About 16.2 cm.

*Inflorescence diameter*.—About 14.1 cm.

*Flower buds*.—Length: About 1.8 cm. Diameter: About 1 cm. Shape: Ovate. Color: Close to 145B to 145C.

*Flower diameter*.—About 6.7 cm.

*Flower depth* (*height*).—About 3 cm.

*Petals*.—Quantity and arrangement: About 15 arranged in several whorls. Length: About 3 cm. Width: About 1.8 cm. Shape: Ovate. Apex: Acute to abruptly acute. Margin: Entire, undulate. Texture, upper and lower surfaces: Smooth, glabrous; slightly velvety. Color: When opening, upper and lower surfaces: Close to 157D; towards the base, close to 149D. Fully opened, upper and lower surfaces: Close to NN155B; towards the base, close to 149D; with development, color becomes closer to 149D.

*Sepals*.—Quantity and arrangement: Five arranged in a single whorl. Length: About 3.6 cm. Width: About 3.7 cm. Shape: Broadly ovate to orbicular. Apex: Rounded to obtuse. Base: Cuneate. Margin: Entire, undulate. Texture, upper and lower surfaces: Smooth, glabrous. Color: When opening and fully opened, upper surface: Close to 157D; towards the base, close to 145C; color becoming closer to 144C with development. When opening and fully opened, lower surface: Close to 145A to 145D.

*Peduncles*.—Length: About 25.2 cm. Diameter: About 5 mm to 7 mm. Strength: Strong. Aspect: About 10° from vertical. Texture: Smooth, glabrous. Color: Close to 144B to 144C.

*Pedicels*.—Length: About 4.8 cm. Diameter: About 3 mm. Aspect: About 30° from peduncle axis. Strength: Moderately strong. Texture: Smooth, glabrous. Color: Close to 144A to 144B.

*Reproductive organs*.—Stamens: Quantity per flower: About 100. Filament length: About 1.4 cm. Filament color: Close to 157D. Anther shape: Reniform, flattened. Anther length: About 2.5 mm. Anther color: Close to 150D. Pollen amount: Scarce. Pollen color: Close to 4D. Pistils: Quantity per flower: About four or five. Pistil length: About 1.1 cm. Stigma shape: Club-shaped. Stigma color: Close to 157D. Style length: About 1 cm. Style color: Close to 150D. Ovary color: Close to 150C to 150D.

*Seeds and fruits*.—Seed and fruit development have not been observed on plants of the new *Helleborus*.

Garden performance: Plants of the new *Helleborus* have been observed to have good garden performance and to tolerate rain, wind, high temperatures of about 35° C. and are hardy to USDA Hardiness Zone 5.

Pathogen & pest resistance: Plants of the new *Helleborus* have not been observed to be resistant to pathogens and pests common to *Helleborus* plants.

It is claimed:

1. A new and distinct *Helleborus* plant named 'NVDH 100' as illustrated and described.

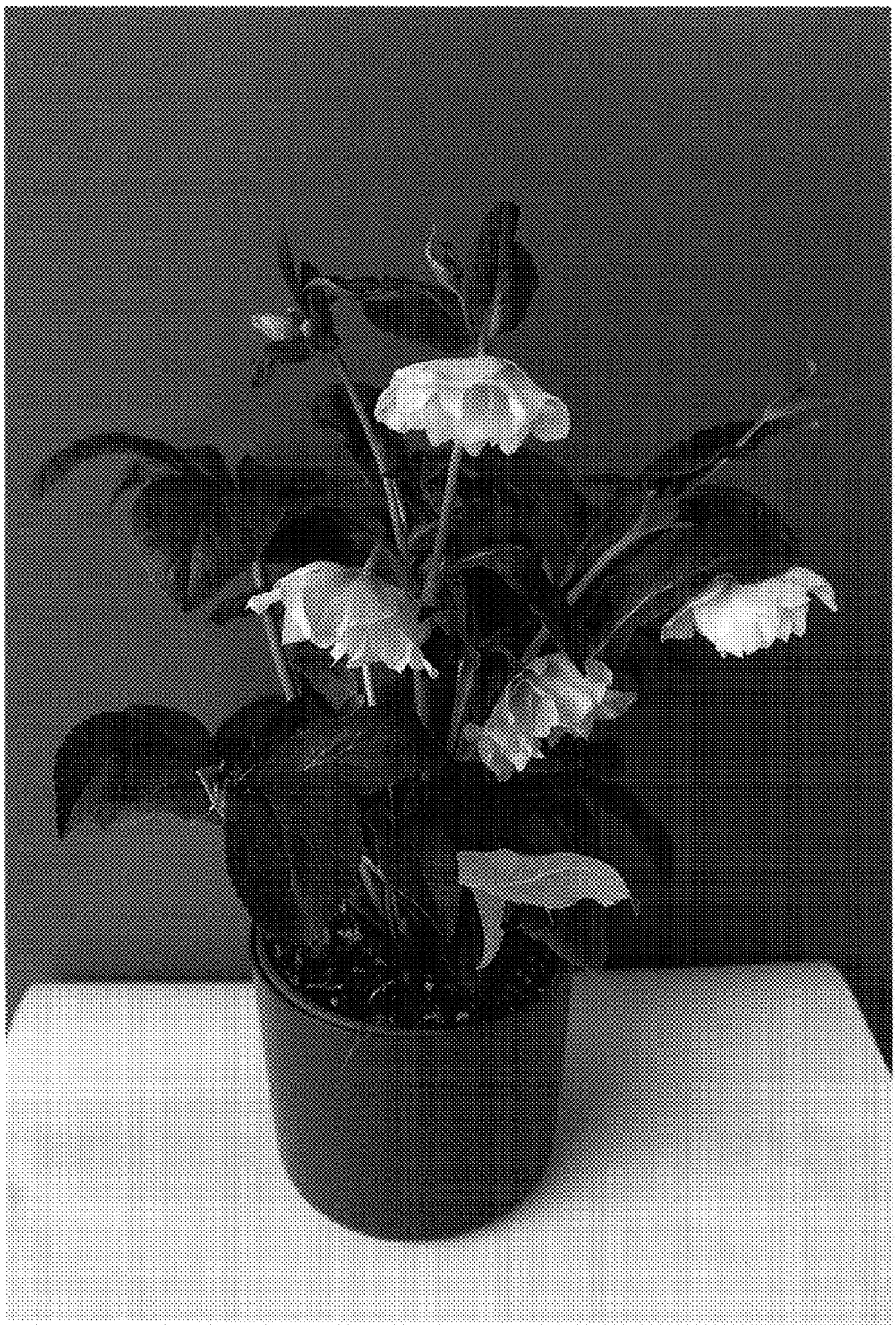

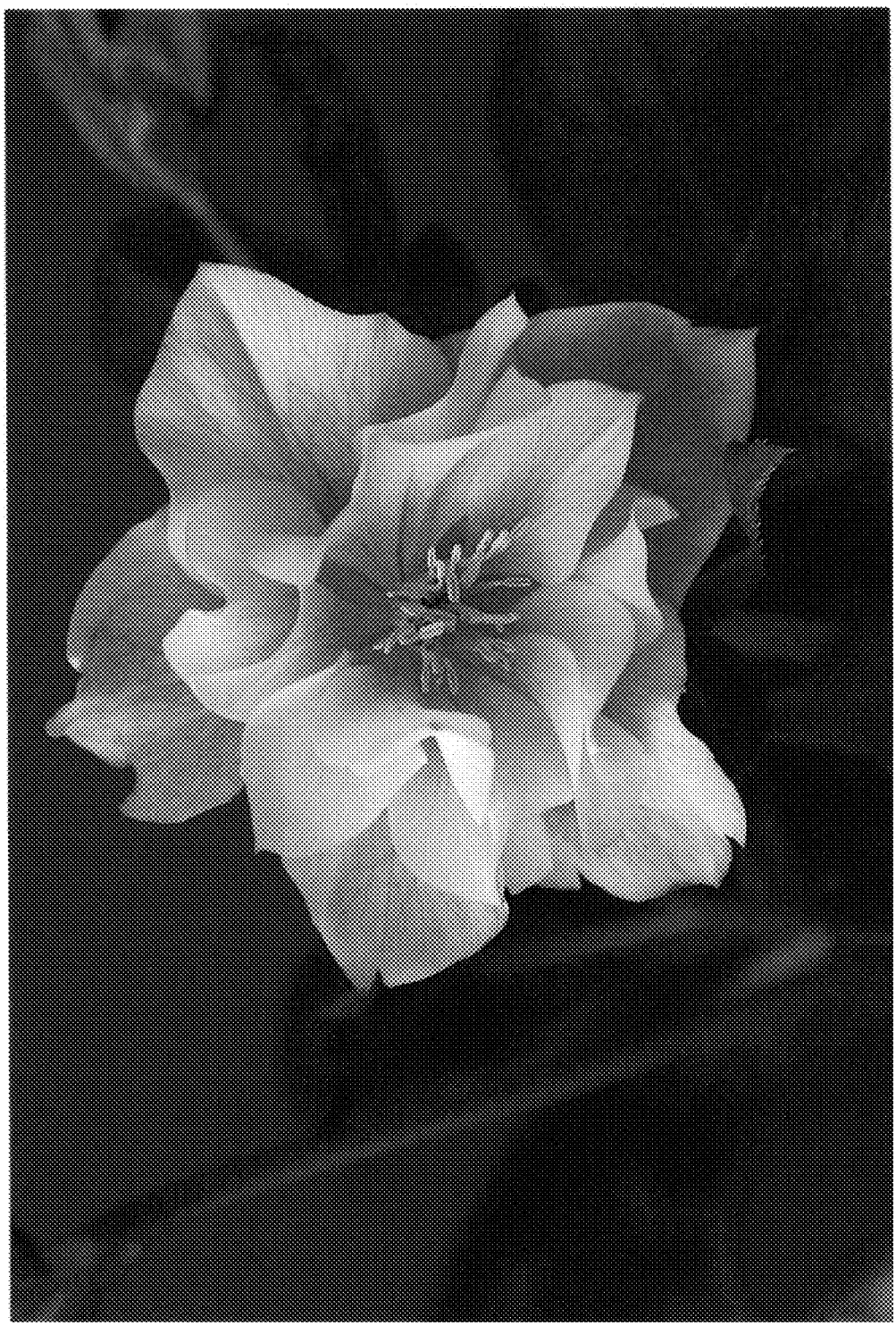

* * * * *